(12) United States Patent
Andrus et al.

(10) Patent No.: US 6,175,006 B1
(45) Date of Patent: *Jan. 16, 2001

(54) AUTOMATED SYSTEM FOR POLYNUCLEOTIDE SYNTHESIS AND PURIFICATION

(75) Inventors: William A. Andrus, San Francisco; Christie D. McCollum, Foster City; Gerald Zon, San Carlos, all of CA (US)

(73) Assignee: The Perkin-Elmer Corporation, Foster City, CA (US)

( * ) Notice: Under 35 U.S.C. 154(b), the term of this patent shall be extended for 0 days.

This patent is subject to a terminal disclaimer.

(21) Appl. No.: 09/281,205

(22) Filed: Mar. 30, 1999

Related U.S. Application Data (60) Continuation of application No. 08/055,464, filed on Apr. 29, 1993, now Pat. No. 5,935,527, which is a division of application No. 07/558,747, filed on Jul. 27, 1990, now Pat. No. 5,262,530, which is a continuation-in-part of application No. 07/287,890, filed on Dec. 21, 1988, now Pat. No. 5,047,524.

(51) Int. Cl.$^7$ .................................................. C07H 21/00

(52) U.S. Cl. .................... 536/25.4; 536/25.3; 536/25.31; 536/25.34; 536/25.41

(58) Field of Search .............................. 536/25.3, 25.31, 536/25.33, 25.34, 25.4, 25.41

(56) References Cited

U.S. PATENT DOCUMENTS

| | | |
|---|---|---|
| 4,373,071 | 2/1983 | Itakura . |
| 4,401,796 | 8/1983 | Itakura et al. . |
| 4,415,732 | 11/1983 | Caruthers . |
| 4,458,066 | 7/1984 | Caruthers et al. . |
| 4,671,941 | 9/1987 | Niina et al. . |
| 4,725,677 | 2/1988 | Koster . |
| 4,816,571 | 3/1989 | Andrus . |
| 4,997,927 | 3/1991 | Blocker et al. . |
| 5,047,524 | * 9/1991 | Andrus et al. . |
| 5,262,530 | * 11/1993 | Andrus et al. . |
| 5,935,527 | * 8/1999 | Andrus et al. . |

FOREIGN PATENT DOCUMENTS

| | | |
|---|---|---|
| 056721A2 | 7/1982 | (EP) . |
| 196101B1 | 10/1982 | (EP) . |
| 219342B1 | 4/1987 | (EP) . |
| WO 82/03079 | 9/1982 | (WO) . |

OTHER PUBLICATIONS

Amarnath V., et al., "Chemical Synthesis of Oligonucleotides," *Chem. Rev.* 77(2):183–217 (1977).

Beaucage, S.L., et al., "Advances in the Synthesis of Oligonucleotides by the Phosphoramidite Approach, *Tetrahedron Report*," vol. 46, No. 12, pp. 2223–2311 (1992).

Caruthers, M.H., et al., "New Methods for Synthesizing Deoxyoligonucleotides," In Setlow, et al., Eds., *Genetic Engineering*, vol. 4 pp. 1–17 (1982).

Dupont Nensorb Product Bulletin, May, 1987 & Nensorb Instruction Manual, Jun. 8, 1987.

Froehler, B.C., et al., "Synthesis of DNA via deoxynucleoside H–phosphonate intermediates," *Nucleic Acids Res.* 14(13):5399–5407 (1986).

Gait, Polymer Supported Synthesis of Oligonucleotides, pp. 1–74, John Wiley & Sons, 1980.

Germann, M.W., et al. "A General Method for the Purification of Synthetic Oligodeoxyribonucleotides Containing Strong Secondary Structure by Reversed–Phase High–Performance Liquid Chromatography on PRP–1 Resin," *Anal. Biochem.* 165:399–405 (1987).

Ikuta, S., et al., "Reverse–Phase Polystyrene Column for Purification and Analysis of DNA Oligomers," *Anal. Chem.* 56:2253–2256 (1984).

H. Koster & S. Geussenhaier: "A Novel Carrier for the Solid Phase Synthesis of Oligomers," *Angewandte Chemie. International Edition.*, vol. 11, No. 8, 1972 Weinheim DE, pp. 713–714.

Pon et al., "Derivatization of Controlled Pore Glass Beads for Solid Phase Oligonucleotide Synthesis," *Biotechniques*, vol. 6, pp. 768–775, (1988).

Wallace et al., "Solid Phase Synthesis & Biological Applications of Poly–deoxyribonucleotides," pp. 631–663, John Wiley & Sons, 1982.

* cited by examiner

Primary Examiner—James O. Wilson
(74) Attorney, Agent, or Firm—Vincent M. Powers; Stephen C. Macevicz (57) ABSTRACT

A method and system for polynucleotide synthesis are provided which employ solid phase synthesis on a non-swellable porous polystyrene support by phosphoramidite or hydrogen phosphonate chemistries. The polystyrene support gives rise to fewer tritylated failure sequences caused by chain growth from extraneous support sites, and allows lower amounts of monomer reactants to be used to achieve equal or better coupling efficiencies as those achieveable with CPG. The method and system also employ nucleoside intermediates whose exocyclic amines are protected by base-labile groups which permit simultaneous cleavage and deprotection of the completed polynucleotide chain in the presence of the solid phase support. This latter feature allows practical automation of both the synthesis and purification of polynucleotides.

12 Claims, 3 Drawing Sheets

AUTOMATED SYSTEM FOR POLYNUCLEOTIDE SYNTHESIS AND PURIFICATION

This application is a continuation of Ser. No. 08/055,464 filed Apr. 29, 1993, which is a divisional of Ser. No. 07/558,747 filed Jul. 27, 1990, now U.S. Pat. No. 5,262,530, which is a continuation-in-part of Ser. No. 07/287,890 Filed Dec. 21, 1988, now U.S. Pat. No. 5,047,524, herein incorporated by reference.

FIELD OF THE INVENTION

The present invention relates generally to the synthesis and purification of polynucleotides, and more particularly, to automated techniques for solid phase synthesis and purification of polynucleotides using phosphoramidite and/or hydrogen phosphonate chemistries.

A key factor in the recent advances in molecular biology has been the development of reliable and convenient methods for synthesizing polynucleotides, e.g. Itakura, *Science*, Vol. 209, pgs. 1401–1405 (1980); and Wallace et al, pgs. 631–663, in Scouten, ed. *Solid Phase Biochemistry* (John Wiley & Sons, New York, 1982). As the use of synthetic polynucleotides has increased, the demand for even greater convenience in the preparation of pure, ready-to-use polynucleotides has also increased. This demand has stimulated the development of many improvements in the basic procedures for solid phase synthesis, e.g. Sinha et al, *Nucleic Acids Research*, Vol. 12, pgs. 4539–4557 (1984)(beta-cyanoethyl in phosphoramidite chemistries); Froehler et al, *Tetrahedron Letters*, Vol. 27, pgs. 469–472 (1986)(H-phosphonate chemistry); Germann et al, *Anal. Biochem.*, Vol. 165, pgs. 399–405 (1987); and Ikuta et al, *Anal. Chem.*, Vol. 56, pgs. 2253–2256 (1984)(rapid purification of synthetic oligonuclectides by way of trityl moieties); Molko et al, European patent publication 241363 dated 3 Apr. 1987 (improved base-labile acyl protection groups for exocyclic amines), and the like.

In spite of such progress, difficulties are still encountered in current methods of polynucleotide synthesis and purification. For example, H-phosphonate and phosphoramidite monomers readily degrade in the presence of even trace amounts of water. This contributes greatly to their very short in-solution shelf lives, and the need to use large molar excesses of reactants to drive the coupling reactions to completion in reasonable times. The presence of water-degraded reactants leads to less pure final products and to more expensive syntheses. This problem is particularly acute for large scale (milligram and greater) syntheses, as well as for small scale (less than 1 umole) syntheses. In the case of the former, the cost of the monomeric reactants makes up the greatest portion of the overall cost of synthesis. Any reduction in the excess molar amount of reactants needed to adequately drive the coupling reaction would lead to substantial cost reductions in the synthesis of large amounts of polynucleotides, e.g. the milligram and gram quantities contemplated for therapeutic use. In the case of the latter, degradation of the reactants by trace amounts of water limits the efficiency that can be achieved on currently available commercial synthesizers, and increases the cost of synthesis because greater amounts of reactant must be used to counter losses due to water and oxygen present in trace amounts in the solvents, tubing, and vessels, or due to water and oxygen leaking into the system from faulty connections, valves, and the like.

As a further example, derivatized controlled pore glass (CPG), the current support of choice in most solid phase methodologies, can be responsible for spurious indications of coupling yields, e.g. Pon et al, *BioTechniques*, Vol. 6, pgs. 768–775 (1988). Moreover, CPG, like most glasses, lacks chemical stability in some of the highly corrosive deprotection reagents, such as concentrated ammonia and trichloroacetic acid, used in polynucleotide synthesis. As a consequence, the CPG support itself can be degraded in the deprotection steps and can be a source of contamination of the final product. This problem is exacerbated by the relative long reaction times required to remove currently used protection groups for exocyclic amines. An extended period of deprotection is required to remove these groups after the polynucleotide has been cleaved from the solid phase support. Thus, complete automation of synthesis and purification has been impractical. Another problem with CPG is that its surface supports chain growth at sites other than those associated with the 5' terminus of an attached nucleoside. Such "extraneous" chain growth gives rise to a heterogeneous population of 5'-blocked (usually tritylated) polynucleotides. Typically, the "extraneous" tritylated products lack one or more 3' nucleotides. This, of course, prevents one from successfully taking advantage of the relatively high hydrophobicity of the trityl group to purify "correct sequence" polynucleotides. Incorrect-sequence extraneous chains are also tritylated. Finally, the hydrophilic nature of CPG causes it to absorb water present in trace amounts in the solvents, which leads to the degradation of the highly water-sensitive monomeric reactants.

In view of the above, the field of solid phase polynucleotide synthesis could be significantly advanced by the availability of alternative support materials (i) which have the favorable mechanical properties of CPG, but which also possess greater chemical stability under the reaction conditions of polynucleotide synthesis, (ii) which provide less opportunity for extraneous chain growth during synthesis, and (iii) which would permit more efficient syntheses, particularly under conditions of reduced molar excess of reactants. The use of such materials coupled with improved exocyclic protection groups would not only allow practical automation of polynucleotide synthesis and purification in a single instrument, but also would permit more efficient and less expensive syntheses of polynucleotides and their derivatives.

SUMMARY OF THE INVENTION

The invention is directed to a system and method for solid phase polynucleotide synthesis on a nonswellable porous polystyrene support by H-phosphonate and/or phosphoramidite chemistries. The use of the polystyrene support (1) significantly reduces the number of failure sequences caused by extraneous initiation of polynucleotide chain growth on the support material, (2) permits deprotection of the polynucleotide product in the presence of the support material by virtue of its superior stability in the presence of deprotection reagents, and (3) permits more efficient syntheses, particularly under conditions of reduced molar excess of the monomeric reactants.

As used herein, "nonswellable" means that the porous polystyrene material remains substantially mechanically rigid, in particular does not increase in volume, when exposed to solvents, reactants, and products of the phosphoramidite and/or hydrogen phosphonate chemistries. Preferably, "nonswellable" means that the volume of the porous polystyrene support increases in volume no more than 5–10% over its dry volume when exposed to the solvents, reactants, and products of the phosphoramidite and/or hydrogen phosphonate chemistries. Mechanical rigidity is desirable for efficient and uniform transfer of reagents to the polynuclectide chain during synthesis.

An important feature of the invention is efficient monomer coupling to the growing polynucleotide chains under conditions of reduced molar excess of monomer over polynucleotide. It is believed that the increased efficiency results from the hydrophobic nature of the nonswellable porous polystyrene support, which unlike CPG does not accumulate moisture, even over many coupling cycles. In particular, with the use of the nonswellable porous polystyrene supports, much lower amounts of reactants are required for achieving equivalent effective reactant concentrations adjacent to the growing polynucleotide as those achieveable with CPG.

Preferably, the correct-sequence polynucleotides synthesized by the method of the invention are purified from the crude mixture cleaved from the reaction column by passage of the crude mixture over an adsorbent which preferentially adsorbs the 5'-blocking group of the correct-sequence polynucleotides. More preferably, whenever the 5'-blocking group is a trityl, the adsorbent is a nonswellable polystyrene solid.

DETAILED DESCRIPTION OF THE INVENTION

The invention is a method and system for producing oligonucleotides and/or polynucleotides of a predetermined sequence. The method comprises the steps of (i) providing a nonswellable porous polystyrene support, (ii) providing a 5'-blocked protected nucleoside having a 3'-hydroxyl and a 5'-hydroxyl, the 5'-blocked protected nucleoside being attached to the nonswellable porous polystyrene support, usually by a base-labile linkage between the 3'-hydroxyl of the protected nucleoside and the support, such that the 5'-blocked protected nucleoside forms a protected correct-sequence chain; (iii) deblocking the 5'-hydroxyl of the correct-sequence chain; (iv) reacting with the 5'-hydroxyl of the correct-sequence chain a 5'-blocked protected nucleoside monomer selected from the group consisting of 5'-blocked protected nucleoside-3'-phosphoramidites and 5'-blocked protected nucleoside-3'-H-phosphonates to form either a protected correct-sequence chain or a failure sequence, the failure sequence having a 5'-hydroxyl; (v) capping the failure sequence by reacting a capping agent with the 5'-hydroxyl of the failure sequence; (vi) repeating steps (iii)–(v) until the polynucleotide of the predetermined sequence is obtained; and (vii) deprotecting the exocyclic amines of the polynucleotide and cleaving the polynucleotide from the nonswellable porous polystyrene support to form a cleavage mixture.

Preferably, the method further includes the step of purifying the polynucleotide from the cleavage mixture. More preferably, the step of purifying includes the steps of exposing the cleavage mixture to a highly crosslinked polystyrene adsorbent, separating the blocked polynucleotide from the failure sequences by washing the polystyrene absorbent to preferentially remove the failure sequences, deblocking the 5'-hydroxyl of the polynucleotide, and eluting the polynucleotide from the polystyrene adsorbent.

Preferably, the step of reacting includes the step of oxidizing the internucleoside phosphorous from the trivalent to the pentavalent state in the phosphoramidite chemistry. Preferably, the method includes the further step of oxidizing the internucleotide phosphorous from the trivalent to the pentavalent state prior to the step of deprotecting in the H-phosphonate chemistry. In further preference, the step of reacting includes delivering the 5'-blocked protected nucleoside monomers to the nonswellable porous polystyrene support in less than or equal to ten fold molar excess of the correct-sequence chains. In still further preference, in small scale syntheses less than or equal to 4 mg of monomer is reacted with the correct-sequence chain. As used herein, "small scale synthesis" means less than or equal to 1 umole of initial nucleoside being attached to the nonswellable porous polystyrene support and the reaction volume being between about 50–200 uL.

As used herein, the term polynucleotide refers to a single stranded chain of either deoxyribonucleotides or ribonucleotides having from a few, e.g. 2–20, to many, e.g. 20 to several hundred or more, nuclectides. The term also includes chains of nucleosides linked by analogs of the phosphate bond, e.g. thiophosphates, and the like.

Detailed procedures for the phosphoramidite and hydrogen phosphonate methods of polynucleotide synthesis are described in the following references, which are incorporated by reference: Caruthers et al, U.S. Pat. Nos. 4,458,066 and 4,500,707; Koester et al, U.S. Pat. No. 4,725,677; Matteucci et al, *J. Amer. Chem. Soc.*, Vol. 103, pgs. 3185–3191 (1981); Caruthers et al, *Genetic Engineering*, Vol. 4, pgs. 1–17 (198 ); Jones, chapter 2, and Atkinson et al, chapter 3, in Gait, ed., *Oligonucleotide Synthesis: A Practical Approach* (IRL Press, Washington, D.C., 1984); Froehler et al, *Tetrahedron Letters*, Vol. 27, Pgs. 469–472 (1986); Garegg et al, *Tetrahedron Letters*, Vol. 27, pgs. 4051–4054 and 4055–4058 (1986); Froehler et al, *Nucleic Acids Research*, Vol. 14, pgs. 5399–5407 (1986); Usman et al, *J. Am. Chem. Soc.*, Vol. 109, pgs. 7845–7854 (1987); Froehler, *Tetrahedron Letters*, Vol. 27, pgs. 5575–5578 (1986); Andrus et al, *Tetrahedron Letters*, Vol. 29, pgs 861–864 (1988); Brill et al, J. Am. Chem. Soc., Vol. 111, pg. 2321 (1989); and Mori et al, Nucleic Acids Research, Vol. 17, pgs. 8207–8219 (1989).

An important feature of the invention is the use of a nonswellable porous polystyrene support for synthesis. Nonswellability of the porous polystyrene depends directly on the degree of crosslinking among the styrene polymers. Such crosslinking is usually measured by a crosslink ratio, which is the molar ratio of crosslinking material (e.g. divinylbenzene) and chain material (e.g. styrene). Preferably, the nonswellable porous polystyrenes of the invention have a crosslink ratio in the range of about 10–60 percent; more preferably, they have a crosslink ratio of about 20–50 percent; and most preferably, they have a crosslink ratio of about 30–50 percent.

As used herein, "porous" means that the nonswellable polystyrene contains pores having substantially uniform diameters in the range of between $100-4000 \times 10^{-8}$ cm. Preferably, the pore diameters are about $1000 \times 10^{-8}$ cm. Several different means are available for manufacturing porous polystyrene solids. As used herein, the term "porous" includes, but is not limited to, so-called macroporous polystyrenes and so-called macroreticular polystyrenes. These materials are widely available commercially in a variety of shapes and sizes, e.g. Polymer Laboratories, Ltd. (Shropshire, United Kingdom); Hamilton Co. (Reno, Nev.), or the like, and are described in U.S. Pat. No. 4,297,220, which is incorporated by reference. Preferably, the non-swellable porous polystyrene supports are used in the form of beads having a diameter in the range of $15-100 \times 10^{-4}$ cm, and more preferably, in the range of $50-70 \times 10^{-4}$ cm.

Prior to its use in synthesis, the nonswellable porous polystyrene-must be linked to a 5'-blocked protected nucleoside, which forms the first nucleoside of the polynucleotide to be synthesized. The nature of this linkage, the 5'-blocking agent, and the protecting groups of the exocyclic amines and internucleoside phosphorous are important features of the invention. Preferably, the first 5'-blocked protected nucleoside is linked to the polystyrene support by way of a base-labile linkage. More preferably, this linkage is an aminomethylsuccinate group, as is commonly used in phosphite triester synthesis, e.g. Atkinson et al, pgs. 45–49, in Gait, ed. *Oligonucleotide Synthesis: A Practical Approach* (IRL Press, Oxford, 1984). The linkage is formed by reacting a 5'-blocked protected nucleoside-'3-O-succinate with an amino-derivatized polystyrene support. Synthesis of the 5'-blocked protected nucleoside-3'-O-succinate is well known in the art, e.g. Atkinson et al, pgs. 47–49 (cited above); and U.S. Pat. No. 4,458,066. Accordingly, these references are incorporated by reference.

As used herein, "5'-blocked" refers to a group attached to the 5'-hydroxyl of either the monomeric nucleoside intermediates used in the invention, or the correct-sequence chain of protected nucleosides. (However, note that chains initiated at "extraneous" sites can be 5'-blocked and yet not be of the correct sequence). Selection of the 5'-blocking group is constrained by three criteria: (i) it must mask the 5'-hydroxyl of the monomer so that it does not compete with the 5'-hydroxyls of the correct-sequence chains during the monomer addition steps, (ii) it must be acid-labile, in that it can be removed so as to expose the 5'-hydroxyl upon mild acid treatment, and (iii) it must be sufficiently hydrophobic to allow 5'-blocked correct-sequence chains to be preferentially adsorbed onto a polystyrene adsorbent over unblocked failure sequences. Preferably, the 5'-hydroxyls are protected as trityl ethers. That is, the 5'-hydroxyl blocking agent, or group, is a trityl. Most preferably, the blocking group is 4,4'-dimethoxytrityl. Synthesis of 5'-blocked nucleoside intermediates is well know in the art, e.g. Froehler et al (cited above), and Caruthers et al (U.S. patents cited above). The trityl blocking groups are removed, that is, the 5'-hydroxyls are "deblocked" by exposure to a mild protic acid. Several trityl deblocking reagents have been used in solid phase polynucleotide synthesis, e.g. Caruthers et al, *Genetic Engineering*, Vol. 4, pgs. 1–17 (1984). Preferably, deblocking is accomplished by exposure to 2% trichloroacetic acid for about 3 minutes at room temperature.

As used herein, "protected" in reference to the monomeric nucleoside intermediates and the correct-sequence chains means (i) that the exocyclic amines of either compound have been acylated with a protection group that prevents the exocyclic amine from participating in the synthetic reaction steps, and (ii) that the internucleoside phosphorous of phosphoramidite intermediates are masked by a base-labile protection group. Preferably, the phosphorous protection group is beta-cyanoethyl, as disclosed by Koester et al, U.S. Pat. No. 4,725,677. Many acyl protection groups are available for use in the invention, e.g. Jones, pgs. 23–34, in Gait, ed. (cited above). Preferably, the exocyclic amine protection groups are sufficiently base-labile so that the correct-sequence chains can be deprotected and cleaved from the polystyrene support in the same reaction step. Preferably, the exocyclic amines of the monomeric nucleoside intermediates are protected by acyl protection groups of the form —COCHR$_1$R$_2$, wherein R$_1$ is H or lower alkyl, and R$_2$ is H, lower alkyl, lower alkoxy, lower aryloxy, or substituted-lower aryloxy. Preferably, the substituents of the lower aryloxy are electron-withdrawing, such as nitro-, cyano-, or sulfonate.

As used herein, the term lower alkyl refers to straight-chained, branched, or cyclic alkyls containing from 1 to 6 carbon atoms. Preferably, the term lower alkoxy refers to methoxy, ethoxy, isopropoxy, tert-butyloxy, or the like. Preferably, the term lower aryloxy refers to phenoxy, napthoxy, biphenyloxy, or the like.

"Electron-withdrawing" denotes the tendency of a substituent to attract valence electrons of the molecule of which it is apart, i.e. it is electronegative, March, *Advanced Organic Chemistry*, pgs. 16–18 (John Wiley, New York, 1985).

These acyl protection groups, when used with the polystyrene supports of the invention, allow deprotection of the exocyclic amines and cleavage of the polynucleotide product from the solid phase support in a single step. Moreover, when beta-cyanoethyl protection groups are employed in the phosphoramidite approach, deprotection of the internucleoside phosphates can also be effected. The single deprotection/cleavage step occurs rapidly enough so that the entire synthesis-purification procedure can be practically automated.

Briefly, the groups are attached to the monomeric nucleoside intermediates by acylation of the exocyclic amino groups of the bases (adenine, guanine, and cytidine) of the deoxynucleosides 2'-deoxyadenosine, 2'-deoxyguanosine, and 2'-deoxycytosine, or of the ribonucleosides, adenosine, guanosine, and cytosine. Thymidine and uridine do not need base protection. Acylation occurs by reacting the acid chloride, such as methoxyacetyl chloride, isobutyryl chloride, or phenoxyacetyl chloride, or the acid anhydride, such as methoxyacetic anhdride, isobutyric anhydride, or phenoxyacetic anhydride, with the 3',5' protected nucleosides. The 3' and 5' protecting groups can be either trimethylsilyl or dimethoxytrityl. The trimethylsilyl groups are applied with either hexamethyldisilazane or trimethylsilyl chloride and can be removed under mild conditions with a neutral aqueous treatment. The dimethoxytrityl group can be applied with dimethoxytrityl chloride either before or after acylation. After acylation protection of the amino group and 5' dimethoxytritylation, the 3' hydroxyl group is converted to a phosphoramidite moiety. This phosphitylation is achieved typically with bis(diisopropylamino)methoxyphosphine or bis(diisopropylamino)cyanoethoxyphosphine with catalysis by diisopropylammonium tetrazolide to give the methyl or cyanoethyl phosphoramidite nucleosides, respectively, as shown by Formula I.

Formula I

Here, $R_1$ and $R_2$ are as described above. DMT represents dimethoxytrityl. B represents adenine, guanine, thymidine, or cytidine. R' represents methyl or beta-cyanoethyl. And iPr is isopropyl. With the above protection group, deprotection and cleavage can be achieved by treatment in concentrated (29%.) ammonia for 6 hours at 20° C., or for 1 hour at 55° C.

As used herein, "correct-sequence chain" refers to a chain of nucleosides which is capable of reacting with an additional monomeric nucleoside intermediate via its 5'-hydroxyl (i.e. it is uncapped) and whose sequence corresponds to that of the desired polynucleotide. The term includes the first nucleoside attached to the solid phase support (i.e. a nucleoside chain of one unit) as well as the completed polynucleotide product of the predetermined sequence. As used herein, "failure sequence" refers to chains of nucleosides which have not reacted with a monomeric nucleoside intermediate during an addition step and which are subsequently capped. The term also includes polynucleotide chains whose growth was initiated at an extraneous site of the solid phase support.

Thiophosphate analogs of polynucleotides can be synthesized in accordance with the invention following the thionization steps taught by Froehler, *Tetrahedron Letters*, Vol. 27, 5575–5578 (1986), for H-phosphonate chemistry, or the thionizaton steps taught by Stec et al, *J. Am. Chem. Soc.*, Vol. 106, pgs. 6077–6079 (1984), for phosphoramidite chemistry.

The polystyrene support is amino-derivatized by standard procedures, e.g. Wallace et al, pgs. 638–639, in Scouten, ed. *Solid Phase Biochemistry* (cited above). Briefly, hydroxymethylpthalimide is reacted with the polystyrene support with a catalytic amount of methylsulfonic acid to form pthalimidomethyl polystyrene. This material is treated with hydrazine to remove the pthalimide protecting group and give aminomethylated polystyrene. The amino loading varies from 20–60 umoles of amino functionality per gram of nonswellable porous polystyrene. This level can be controlled by adjusting the concentrations of the reagents and reaction time.

This material is then reacted with the 5'-blocked protected nucleoside-3'-O-succinate. Unreacted amine of the polystyrene are rendered inactive by acylation with a moncarboxylic acid, e.g. as disclosed in U.S. Pat. No. 4,458,066. Preferably, the amines are rendered inactive by acetylation with acetic anhydride.

As outlined above, synthesis of the desired polynucleotide usually proceeds by repeated cycles of deblocking, monomer addition, and capping until synthesis is complete. As used herein, the term capping refers to reacting either the free 5' hydroxyl of a 3' to 5' growing nucleotide chain or the free 3' hydroxyl of a 5' to 3' growing nucleotide chain with a capping agent to render the chain incapable of participating in subsequent condensation steps. The preferred capping agents of the invention are phosphite monoesters of the form:

Formula II wherein R, either alone or together with the oxygen to which it is attached, is unreactive with the reagents used in solid phase oligonucleotide synthesis, particularly phosphoramidites or nucleoside hydrogen phosphonates. Preferably, R represents a lower alkyl, an electron-withdrawing substituted lower alkyl, a lower alkyl- or halo-substituted aryl, or a heterocycle containing nitrogen, oxygen, or sulfur and from 5–8 carbon atoms. More preferably, R is methyl, ethyl, propyl, isopropyl, n-butyl, sec-butyl, tert-butyl, n-pentyl, cyclopentylmethyl, isopentyl, neopentyl, n-hexyl, neohexyl, isohexyl, cyclohexylmethyl, beta-cyclopentylethyl, lower alkyl- or halo-substituted phenyl, lower alkyl- or halo-substituted benzyl, or lower alkyl- or halo-substituted phenylethyl, morpholinyl, thiomorpholinyl, piperidinyl, piperazinyl, beta-electron-withdrawing-substituted ethyl, or the like. In further preference, the electron-withdrawing substituent of beta-electron-withdrawing-substituted ethyl is cyano, nitro, phenylsulphonyl, or phenylester. Most preferably, the beta-electron-withdrawing-substituted ethyl is beta- cyanoethyl. In further preference, the lower alkyl- or halo-substituents of the lower alkyl- or halo-substituted phenyl and benzyl are methyl, chloro, or bromo. In further preference, morpholinyl, thiomorpholinyl, and piperidinyl are morpholino, thiomorpholino, and piperidino, respectively.

The chemical structures illustrated by Formula II are referred to in the literature as both phosphites and phosphonates. Reflecting the approximate usage in the literature, the structures will be referred to herein as phosphites, except when R is a nucleoside. In such cases the structure will be referred to as a hydrogen or H- phosphonate.

As illustrated by Formula III, the capping method of the invention comprises reacting a phosphite monoester defined by Formula II, 1, with the free 5' or 3' hydroxyl of a failure sequence, 2, in the presence of a sterically hindered acid chloride, 3, to form a phosphite diester, 4, between the failure sequence and a group which is inert to subsequent reaction steps.

Formula III

-continued

4

Z = H, OH
B = purine, pyrimidine

Preferably, the capping agents of the invention (1 in Formula IV below) are prepared by alkaline hydrolysis of the symmetrical phosphite diesters, 5, as described by Gibbs et al in *Synthesis*, pgs. 410–413 (1984), which is incorporated by reference. The phosphite monoester 1 can be used directly as a salt after evaporating volatile by-products Of the reaction or after purification by conventional means.

Formula IV

In the sterically hindered acid chloride 3, R' is preferably tert-butyl, sec-butyl, cyclohexyl, adamantyl, norbornyl, phenyl, aryl, or the like. More preferably, R' is tert-butyl, norbornyl, or adamantyl. Most preferably, R' is adamantyl.

Preferably, $X^+$ is ammonium, lower alkylammonium, pyridinium, lutidinium, cyclohexylammonium, 1,8-diazabicyclo[5.4.0]undec-7-ene ammonium, a metal salt cation such as $Na^+, K^+, Li^+, Ba^+, Mg^+$, or the like. More preferably, $X^+$ is triethylammonium, tetrabutylammonium, diisopropylethylammonium, pyridinium, lutidinium, or cyclohexylammonium. Most preferably, $X^+$ is triethylammonium, tetrabutylammonium, or 1,8-diazabicyclo[5.4.0]undec-7-ene ammonium.

Preferably, prior to delivery to the synthesis column bearing the oligonucleotide, a phosphite monoester of the invention and its cationic counter ion are dissolved in a solution comprising an aprotic polar solvent, such as acetonitrile, tetrahydrofuran, dichloromnethane, or the like, or some combination thereof, and a mild base such as pyridine, picoline, lutidine, collidiner or the like. Pyridine is the most preferred mild base. Preferably, the concentration of the phosphite monoester is between about 0.01 to 0.10 molar. Likewise, the sterically hindered acid chloride (3 in Formula III), prior to delivery to the synthesis column, is dissolved in a solution comprising an aprotic polar solvent, such as acetonitrile, tetrahydrofuran, dichloromethane, or the like, or some combination thereof, and a mild base such as pyridine, picoline, lutidine, collidine, or the like. Pyridine is the most preferred mild base. The respective solutions are delivered concurrently to the synthesis column bearing the growing oligonucleotide so that the molar ratio of the phosphite monoester to the sterically hindered acid chloride present in the reaction mixture is about 1:5. This operation can be readily performed by an automated DNA synthesizer, such as the Applied Biosystems models 380A, 380B, or 381A. The capping procedure of the invention is performed as a step in each cycle, after the coupling reaction, to render the failure sequences inert. Preferably, the synthesis column is immersed in the reaction mixture for about 20–120 seconds at room temperature, after which the reagents are flushed from the column with a solvent, such as acetonitrile, tetrahydrofuran, dichloromethane, pyridine, or the like, or some combination thereof. All vessels within the instrument must be maintained rigorously free of moisture and oxygen under an atmosphere of an inert gas, such as argon.

At the completion of synthesis, the polynucleotide chains (both correct-sequence chains and failure sequences) are deprotected and cleaved from the polystyrene support to form a cleavage mixture. Preferably, this is accomplished by treatment with concentrated ammonium hydroxide for 4–5 hours at room temperature or for about 1 hour at 55° C. The cleavage mixture is applied to a solid phase adsorbent that preferentially adsorbs the 5'-blocked deprotected polynucleotides. The preferential adsorption is accomplished by selecting a blocking group and solid phase adsorbent so that they have a strong mutual attraction relative to the rest of the polynucleotide. The attraction can be based on hydrophobicity, charge, or other physiochemical property. Trityl blocking groups are preferentially adsorbed onto a hydrophobic solid phase adsorbent, such as polystyrene. Preferably, whenever trityl blocking groups are used the solid phase adsorbent is a nonswellable porous polystyrene pretreated with a concentrated alkylammonium salt solution. Preferably, the nonswellable porous polystyrene used as the adsorbent is used in the form of beads having a diameter in the range of about $15-100\times10^{-4}$ cm and pore size in the range of 100–1000 angstroms. More preferably, the bead diameter is in the range of $50-70\times10^{-4}$ cm and pore diameter is about 300 angstroms.

Prior to applying the cleavage mixture to the polystyrene adsorbent, the adsorbent is flushed with an organic solvent, such as acetonitrile, to wet the surface, then a concentrated alkylammonium salt solution, preferably a 2M solution of triethylamine acetate, is applied to establish a lipophilic counterion. After the cleavage solution, containing the polynucleotide synthesis mixture in concentrated ammonia, is applied to the polystyrene adsorbent, the adsorbent is then washed, preferably with dilute ammonia (a 3% solution) and water, to remove the failure sequences and other contaminants, the correct-sequence chains are deblocked, i.e. de-tritylated, and the de-tritylated polynucleotide is eluted from the adsorbent. Preferably, the elution is accomplished with a neutral solvent, e.g. 20% acetonitrile in water, or like solvent. By way of example, polystyrene adsorbent (50 milligrams per 5 OD units of oligonucleotide to be purified) is packed in a purification chamber, e.g. a standard flow through chromatography column, with an internal volume of about 500 ul. The polystyrene adsorbent is pre-washed with 5 ml of acetonitrile, then flushed with 5 ml of 2M triethylammonium acetate. The cleavage mixture is slowly forced through the purification chamber manually with a 5 ml syringe at about 2 ml per minute to load the tritylated sequences. After loading, the purification chamber is washed first with 10 ml of 3% ammonia/water and then with 10 ml water. 3 ml of 2% trifluoroacetic acid in water is applied to the purification chamber and allowed to set for 3 minutes, afterwhich 15 ml of water is flushed through the chamber to remove residual acid. Finally, the purified oligonucleotide is eluted from the adsorbent with 1 ml of 20% acetonitrile/water.

Preferably, the method of the invention is automated. The apparatus for automating can take several forms. Generally, the apparatus comprises a series of reagent reservoirs, a synthesis chamber containing the nonswellable porous polystyrene support, a purification chamber (which may be the same or different from the synthesis chamber) containing the solid phase adsorbent, and a computer controlled means for transferring in a predetermined manner reagents from the reagent reservoirs to and from the synthesis chamber and the purification chamber, and from the synthesis chamber to the purification chamber. The computer controlled means for transferring reagents can be implemented by a general purpose laboratory robot, such as that disclosed by Wilson et al, *BioTechniques*, Vol. 6, pg. 779 (1988), or by a dedicated system of tubing, and electronically controlled valves. Preferably, the computer controlled means is implemented by a dedicated system of valves and tubing connecting the various reservoirs and chambers. In further preference, the reagents are driven through the tubing by maintaining a-positive pressure in the reagent reservoirs by means of a pressurized inert gas, such as argon, as is used by many widely available automated synthesizers, e.g. Applied Biosystems, Inc. models 380B or 381A DNA synthesizers.

Figure 1:
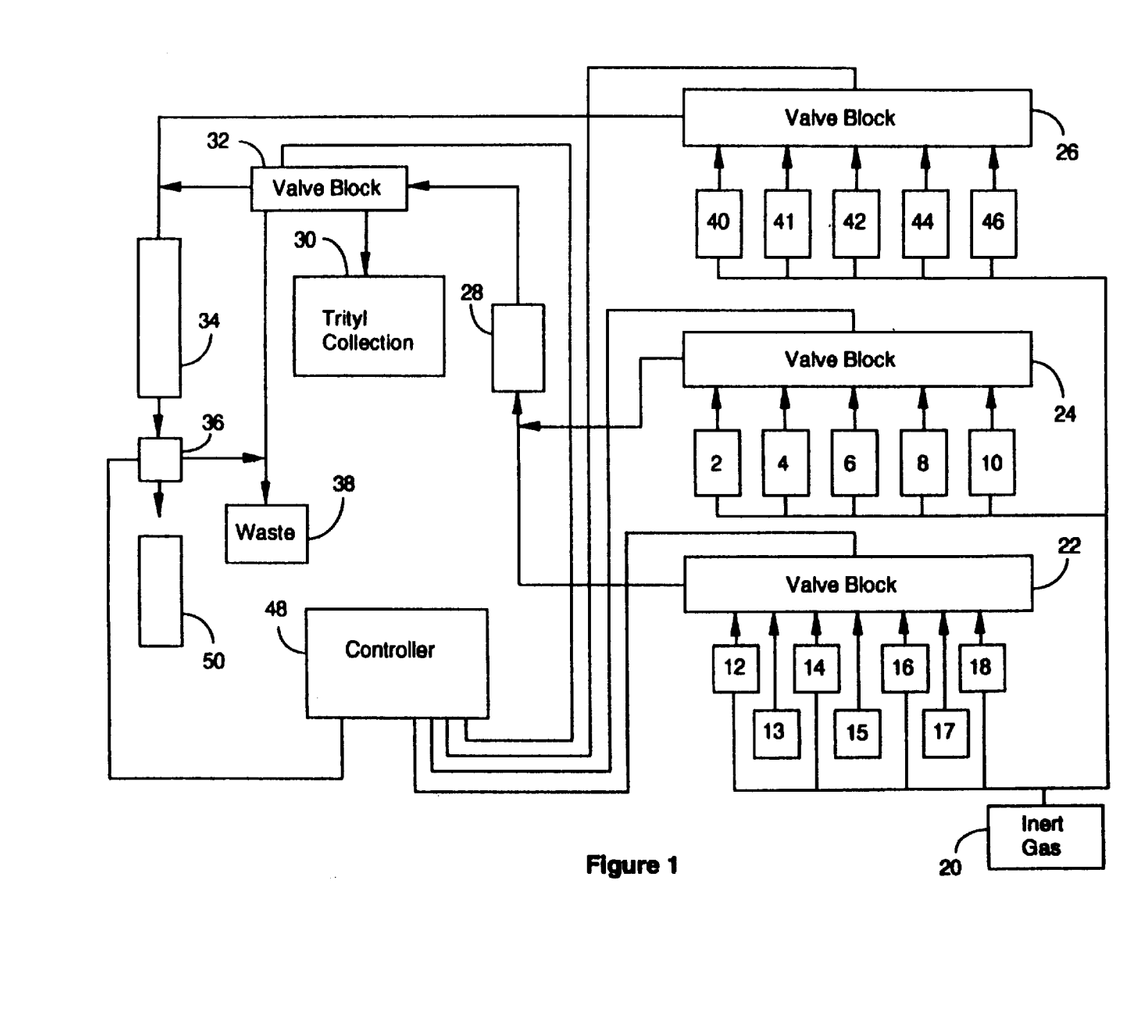
FIG. 1 diagrammatically represents a preferred apparatus for implementing the method of the invention.

A diagrammatic representation of a preferred embodiment of such an apparatus is illustrated in FIG. 1. The apparatus of FIG. 1 is set forth as if the phosphoramidite chemistry were being employed. The same instrument can also be used to automate the H-phosphonate synthesis and purification with obvious modifications, e.g. different synthesis reagents are used, different reaction times are required, and the like. These modifications are readily implemented via programmable controller 48, or like means. 5'-blocked protected nucleoside intermediates are stored in reservoirs 2 through 10, one reservoir each for the four natural nucleosides. Optionally, an additional reservoir 10 is provided for a 5'-blocked protected nucleoside analog, e.g. deoxyinosine, a linking agent, e.g. U.S. Pat. No. 4,757,141, or like intermediates. The reservoirs 2 through 10 containing the synthesis intermediates are connected to synthesis chamber 28 by way of valve block 24 whose operation is controlled by controller 48. Synthesis reagents are stored in reservoirs 12 through 18. For example, in phosphoramidite chemistry these can be 12 trichloroacetic acid in dichloromethane for deblocking, 13 iodine/lutidine/water/tetrahydrofuran solution for oxidizing internucleoside phosphorous, 14 tetrazole/acetonitrile solution for activating the nucleoside intermediates, 15 ammonium hydroxide for cleaving the completed chain from the synthesis support, 16 1-methylimidazole/tetrahydrofuran solution and 17 tetrahydrofuran/lutidine/acetic anhydride solution for capping, and 18 acetonitrile for washing. These reagent reservoirs are connected to synthesis chamber 28 by way of valve block 22 which is controlled by controller 48. Synthesis proceeds under programmed control with each nucleotide being added to the growing chain by successive cycles deblocking, addition, capping, and oxidizing. Reagents removed from synthesis chamber 28 are directed to either trityl collection station 30, waste reservoir 38, or purification chamber 34 by way of valve block 32, which is controlled by controller 48. During each cycle trityl blocking groups released by deblocking are monitored photometrically at trityl collection station 30 to track the efficiency of the synthesis.

When synthesis is complete, the synthesis support is treated with concentrated ammonium hydroxide to deprotect and cleave the polynucleotide chains. Before the resulting solution (the cleavage solution) is transferred to purification chamber 34, the polystyrene adsorbent in the chamber is flushed first with acetonitrile and then with triethylammonium acetate, from reservoirs 40 and 41, respectively. The cleavage mixture is transferred to purification chamber 34 via valve block 32 where it reacts with the polystyrene adsorbent. The polystyrene adsorbent is then treated with a series of purification reagents from reservoirs 40 through 46 to separate failure sequences and impurities from correct-sequence polynucleotides and to elute the correct-sequence polynucleotides from the adsorbent. Transfer of reagents from the reservoirs and to and from the purification chamber 34 are made by way of valve blocks 26 and 36, which are controlled by controller 48. First, dilute ammonium hydroxide from 40 flushes purification chamber 34 to remove capped failure sequences and other contaminants. Next, the tritylated polynucleotides are detritylated by treatment with a 2% trifluoroacetic acid solution in water, reservoir 44, and the the detritylated polynucleotides are eluted with a 20% acetonitrile solution in water, reservoir 42, and are collected in product vessel 50.

The following examples serve to illustrate the present invention and are not to be considered limitations thereof.

EXAMPLES

Example I

Comparison of Extraneous Chain Initiation on CPG and Polystyrene Supports During Synthesis A 5'-tritylated-thymidine-derivatized polystyrene support (4000 angstrom pore size), a 5'-tritylated-thymidine-derivatized CPG support (1000 angstrom pore size), and a 5'-tritylated-thymidine-derivatized CPG support (500 angstrom pore size) were treated with 5'-trityldeoxyadenosine-3'-phosphoramidite (A) and tetrazole activator for one hour and then detritylated. The nucleosidic material was then removed by treating the supports with ammonia, and separately analyzed by HPLC, the pertinent results of which are shown in Table I. Addition of A to the supports can only occur at two types of sites: (i) reactive sites on the support surface which were never capped or became uncapped, or (ii) detritylated thymidine. Reaction at the former sites leads to the detection of adenosine monophosphate (AMP) in the HPLC analysis, and in practice to a heterogeneous population of tritylated polynucleotides cleaved from the synthesis support (as discussed below). Reaction at the latter sites leads to the detection of an A-T dinucleotide in the EPLC analysis. The presence of the latter sites reflects instability of the trityl group during storage. Other compounds detected in the EPLC analysis are thymidine (the predominant component) and benzamide, a by-product of the removal of the protecting group of adenine.

TABLE I

Relative Amounts From Chromatogram Peaks

| Support | AMP | thymidine | benzamide | A-T dimer |
| --- | --- | --- | --- | --- |
| Polystyrene | 1.9% | — | — | 0.4% |
| CPG (1000 angstrom) | 5.7% | — | — | 0.8% |
| CPG (4000 angstrom) | 4.1% | — | — | 2.4% |

The data indicate that the polystyrene support generates less than half the extraneous start sites as does CPG. Therefore, polynucleotides made with the polystyrene support are more pure and can be more easily purified than polynucleotides made on a CPG support.

Example II

Synthesis of an 18-mer Oligonucleotide on CPG and Polystyrene

Three 18-mer oligonucleotides of the same sequence were synthesized on an Applied Biosystems model 380B synthesizer (which has 3 reaction chambers) programmed for using phosphoramidite chemistry, two on CPG supports and the other on a polystyrene support in accordance with the invention (beads from Polymer Laboratories, Ltd., part number 1412-6602, derivatized as described above). All three reaction chambers corresponded to 0.2 umole-scale syntheses and the machine was run in accordance with manufacturer's recommended protocols. The crude product of each synthesis was analysed by capillary electrophoresis on an Applied Biosystems Model 270A instrument. This analysis indicated that peaks corresponding to the correct sequence polynucleotide make up 63% and 73% of the crude product from the CPG-based syntheses, respectively, and 83% of the crude product from the polystyrene-base synthesis.

Example III

Synthesis of a 72-mer Polynucleotide on CPG and Polystyrene

Figure 2A:
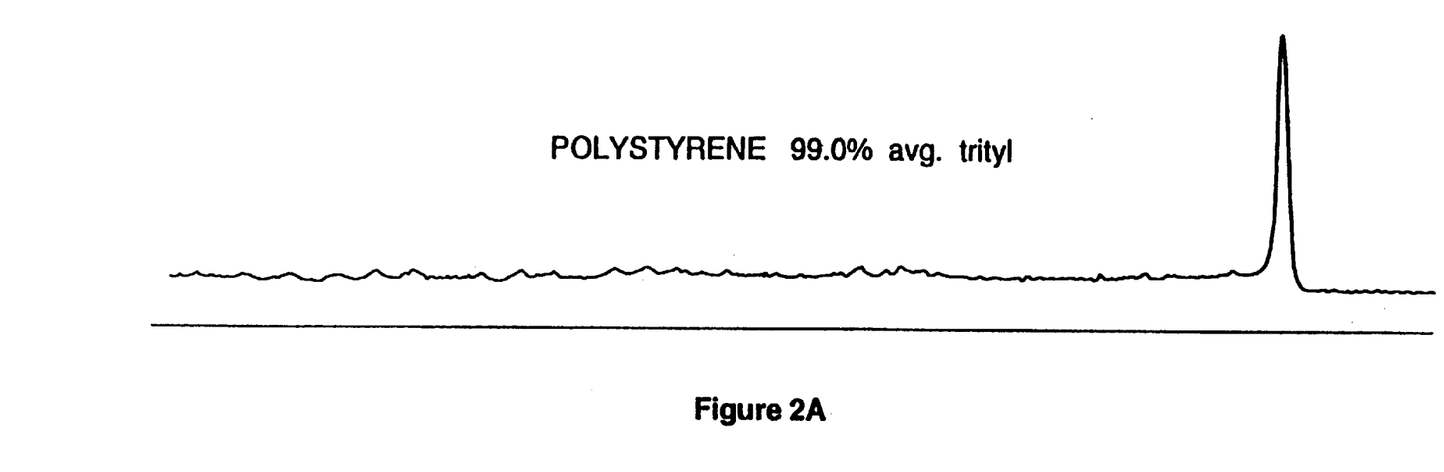
FIG. 2 illustrates a densitometric scan of an autoradiogram of electrophoretically separated components of the crude reaction products of a 72-mer synthesis on a polystyrene support (A) and a CPG support (B).
Figure 2B:
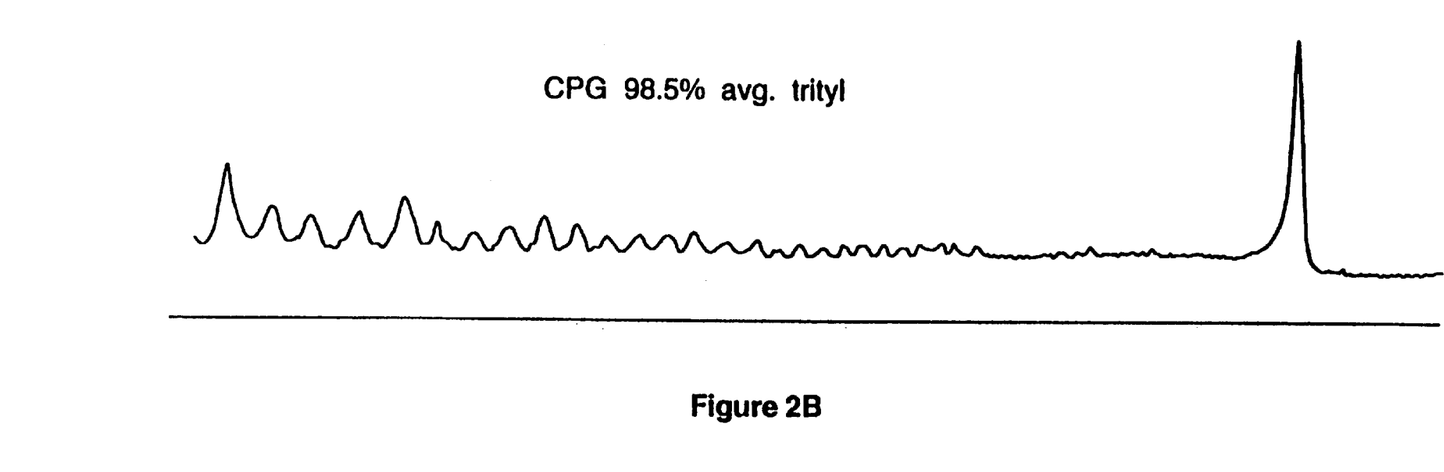

Two 72-mer polynucleotides of the same sequence (base composition $A_{15}C_{20}G_{19}T_{18}$) were synthesized on an Applied Biosystems Model 391 PCR-Mate using the manufacturer's recommended protocols. In one synthesis a polystyrene support was used as described in Example I. In the other synthesis, CPG was used as a support. The crude polynucleotides were radiolabeled with $^{32}$P-ATP, separated by polyacrylamide gel electrophoresis, and autoradiographed. The bands of each lane on the film were quantitated by densitometry. The densitometry profiles are shown in FIGS. 2A and 2B. The largest peak in both Figures corresponds to the 72-mer correct-sequence product. The profiles clearly show larger populations of failure sequences in the crude product of the CPG-based synthesis.

Example IV

Figure 3A:
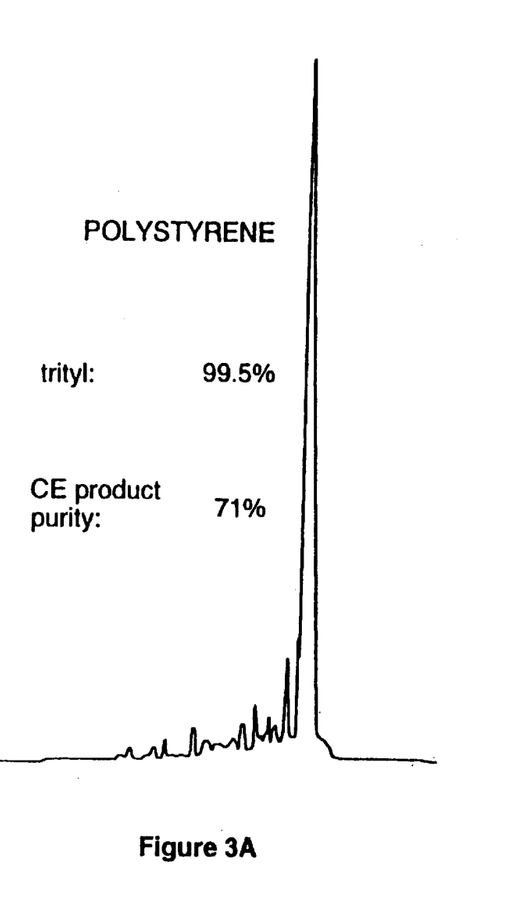
FIGS. 3A and 3B are capillary electrophograms of 21-mer syntheses on polystyrene (A) and CPG (B).
Figure 3B:
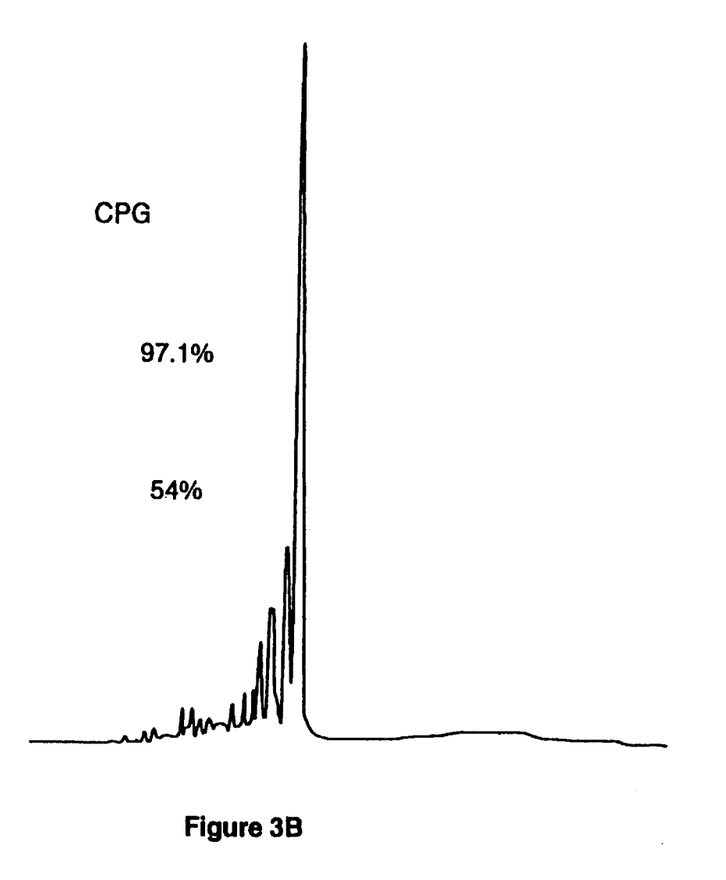

Synthesis of a 21-mer Polynucleotide on Polystyrene and CPG with Limiting Amounts of Monomer Reactant Two sets of identical 21-mer polynucleotides (5'-GTCAGTTCCATCAACATCATT-3') were synthesized concurrently on separate 0.05 umole polystyrene, 0.2 umole polystyrene, and 0.2 umole CPG columns on an Applied Biosystems model 380B DNA synthesizer using the manufacturer's recommended protocol. In the first set, 7.5 mg of phosphoramidite (0.1M) (the amount in the recommended protocol) in solution for 21 days was delivered to the reaction vessel on each coupling cycle. In the second set, 4.0 mg of freshly disolved phosphoramidite monomer (in an approximate 0.05M solution) was delivered to the reaction vessel on each coupling cycle. Otherwise, the synthesis of the two sets of polynucleotides was identical. The crude reaction mixtures and polystyrene adsorbent-purified ("OPC purified") reaction mixtures were analyzed by capillary electrophoresis (CE) using an Applied Biosystems model 270A instrument. As shown by the data in Table II, syntheses on polystyrene resulted in equal or better yields in every case. Moreover, examination of the CE electrophorograms (FIG. 3) suggests that undesired chain growth off the support may contribute to the comparatively high 20-mer (N-1 mer) contamination in the CPG samples. CE analysis of the purified samples indicates that these contaminants are tritylbearing.

TABLE II

| Support | Scale (umole) | Average Trityl Yield | Polynucleotide in Crude Product | Polynuclectide in OPC Product |
|---------|---------------|----------------------|-------------------------------|-------------------------------|
| 21-day-old phosphoramidites 7.5 mg/cycle: | | | | |
| CPG | 0.2 | 98.6% | 65% | 74% |
| PS | 0.2 | 99.3% | 62% | 86% |
| PS | .05 | 99.6% | 74% | 88% |
| Fresh phosphoramidites 4.0 mg/cycle: | | | | |
| CPG | 0.2 | 97.1% | 54% | 71% |
| PS | 0.2 | 99.0% | 62% | 82% |
| PS | .05 | 99.5% | 71% | 88% |

The foregoing disclosure of preferred embodiments of the invention has been presented for purposes of illustration and description. It is not intended to be exhaustive or to limit the invention to the precise form disclosed. Obviously many modifications and variations are possible in light of the above teaching. The embodiments were chosen and described in order to best explain the principles of the invention and its practical application, to thereby enable others skilled in the art to best utilize the invention in various embodiments and with various modifications as are suited to the particular use contemplated. It is intended that the scope of the invention be defined by the claims appended hereto.

We claim:

1. A method for purifying a polynucleotide comprising
    (a) forming a polynucleotide on a solid support by repeated steps of (i) deblocking a 5'-hydroxyl group of a 5'-blocked protected nucleoside having a 3'-hydroxyl and a 5'-hydroxyl, (ii) reacting the deblocked 5'-hydroxyl with a 5'-blocked protected nucleoside monomer selected from the group consisting of 5'-blocked protected nucleoside-3'-phosphoramidite and 5'-blocked protected nucleoside-3'-hydrogen phosphonate to form either a protected correct-sequence polynucleotide chain or a failure sequence, the failure sequence having a 5'-hydroxyl, and (iii) repeating steps (i) and (ii) until a desired polynucleotide is obtained, wherein the solid support comprises a chamber containing (1) a nonswellable porous polystyrene support capable of remaining substantially mechanically rigid during polynucleotide synthesis, and (2) a hydrophobic adsorbent capable of non-covalently adsorbing a tritylated polynucleotide,
    (b) cleaving the polynucleotide from the nonswellable porous polystyrene support to form a cleavage mixture,
    (c) purifying the cleaved polynucleotide from the cleavage mixture by adsorbing the cleaved polynucleotide to the hydrophobic adsorbent and washing the hydrophobic adsorbent to selectively remove unblocked polynucleotides which the cleaved polynucleotide, and
    (d) deblocking the 5'-hydroxyl of the adsorbed polynucleotide to form a deblocked polynucleotide and eluting the deblocked polynucleotide from the hydrophobic adsorbent.

2. The method of claim 1 further including the step of capping said failure sequence by reacting a capping agent with said 5'-hydroxyl of said failure sequence.

3. The method of claim 2 wherein said 5'-blocked protected nucleoside monomer is a 5'-blocked protected nucleoside-3'-hydrogen phosphonate, and wherein said capping occurs after said reacting.

4. The method of claim 2 wherein said 5'-blocked protected nucleoside monomer is a 5'-blocked protected nucleoside-3'-phosphoramidite, and wherein said capping occurs after said reacting.

5. The method of claim 4 wherein said 5'-blocked protected nucleoside-3'-phosphoramidite is defined by the formula:

wherein $R_1$ is hydrogen or lower alkyl, $R_2$ is hydrogen, lower alkyl, lower alkoxy, lower aryloxy, or cyano-, nitro-, or sulfono-substituted lower aryloxy, R' is methyl or beta-cyanoethyl, DMT is dimethoxytrityl, and B is adenine, guanine, thymidine, or cytidine.

6. The method of claim 5 wherein $R_1$ is hydrogen, ethyl, or propyl, and $R_2$ is hydrogen, methyl, ethyl, propyl, methoxy, ethoxy, isopropoxy, tert-butyloxy, phenoxy, napthoxy, or biphenoxy.

7. The method of claim 6 wherein $R_1$ is hydrogen or methyl, and $R_2$ is hydrogen, methyl, ethoxy, or phenoxy.

8. The method of claim 1 wherein said step of reacting further includes exposing said 5'-hydroxyl of said correct-sequence chain to said 5'-blocked protected nucleoside monomer, said 5'-blocked protected nucleoside monomer being in less than or equal to ten molar excess of said 5'-hydroxyl of said correct-sequence chain.

9. The method of claim 8 wherein said 5'-blocked protected nucleoside monomer is a 5'-blocked protected nucleoside-3'-phosphoramidite.

10. The method of claim 1, wherein said hydrophobic adsorbent is a nonswellable porous polystyrene adsorbent.

11. The method of claim 1 wherein said 5'-blocked protected nucleoside monomer is a 5'-blocked protected nucleoside-3'-hydrogen phosphonate.

12. The method of claim 1 wherein said 5'-blocked protected nucleoside monomer is a 5'-blocked protected nucleoside-3'-phosphorarnidite.

* * * * *